(12) United States Patent
Mohr

(10) Patent No.: US 9,636,000 B2
(45) Date of Patent: May 2, 2017

(54) RETRACTION OF TISSUE FOR SINGLE PORT ENTRY, ROBOTICALLY ASSISTED MEDICAL PROCEDURES

(71) Applicant: Intuitive Surgical Operations, Inc., Sunnyvale, CA (US)

(72) Inventor: Catherine J. Mohr, Mountain View, CA (US)

(73) Assignee: Intuitive Surgical Operations, Inc., Sunnyvale, CA (US)

( * ) Notice: Subject to any disclaimer, the term of this patent is extended or adjusted under 35 U.S.C. 154(b) by 143 days.

(21) Appl. No.: 13/958,977

(22) Filed: Aug. 5, 2013

(65) Prior Publication Data

US 2013/0317306 A1 Nov. 28, 2013

Related U.S. Application Data

(62) Division of application No. 11/762,217, filed on Jun. 13, 2007, now Pat. No. 8,517,933.

(Continued)

(51) Int. Cl.
*A61B 17/02* (2006.01)
*A61B 1/00* (2006.01)
(Continued)

(52) U.S. Cl.
CPC ...... *A61B 1/00087* (2013.01); *A61B 1/00082* (2013.01); *A61B 1/313* (2013.01);
(Continued)

(58) Field of Classification Search
CPC . A61B 17/0218; A61B 17/3423; A61B 17/02;
A61B 17/0293; A61B 1/32; A61B 2017/0225; A61B 2017/3445; A61B 17/3462; A61B 17/3431; A61B 17/3439; A61B 2017/3419; A61F 2/958; A61F 2002/9583
(Continued)

(56) References Cited

U.S. PATENT DOCUMENTS 4,447,227 A 5/1984 Kotsanis
4,886,062 A * 12/1989 Wiktor .................... 606/194

(Continued)

FOREIGN PATENT DOCUMENTS

WO WO 2005/006964 A2 * 1/2005

OTHER PUBLICATIONS

Vertut, Jean and Phillipe Coiffet, Robot Technology: Teleoperation and Robotics Evolution and Development, English translation, Prentice-Hall, Inc., Inglewood Cliffs, NJ, USA 1986, vol. 3A, 332 pages.

*Primary Examiner* — Jan Christopher Merene

(57) ABSTRACT

A single port entry surgical instrument has an elongated structure with lumens through which surgical tools and an image capturing device may be inserted and controllably extended out of its distal end for performing a medical procedure, a tubular-shaped balloon disposed around the elongated structure, and an expandable retractor disposed around the balloon so that when the balloon is inflated, the retractor expands and locks in an expanded configuration to retract extraneous tissue. The port entry may be secured using the expandable retractor or sealed using another inflatable balloon disposed around the proximal end of the elongated structure and centered in the port entry.

3 Claims, 10 Drawing Sheets

Related U.S. Application Data

(60) Provisional application No. 60/813,198, filed on Jun. 13, 2006.

(51) Int. Cl.
    *A61B 1/313* (2006.01)
    *A61B 1/32* (2006.01)
    *A61B 34/00* (2016.01)
    *A61B 17/29* (2006.01)
    *A61B 90/00* (2016.01)

(52) U.S. Cl.
    CPC ............ *A61B 1/32* (2013.01); *A61B 17/0218* (2013.01); *A61B 34/70* (2016.02); *A61B 34/72* (2016.02); *A61B 1/00193* (2013.01); *A61B 17/29* (2013.01); *A61B 90/37* (2016.02)

(58) Field of Classification Search
    USPC ................................................ 600/206, 207
    See application file for complete search history.

(56) References Cited

U.S. PATENT DOCUMENTS

| | | | |
|---|---|---|---|
| 5,116,318 A * | 5/1992 | Hillstead | A61F 2/90 604/103.05 |
| 5,197,978 A * | 3/1993 | Hess | A61F 2/82 606/194 |
| 5,328,469 A * | 7/1994 | Coletti | A61M 25/104 604/103.09 |
| 5,345,927 A | 9/1994 | Bonutti | |
| 5,361,752 A | 11/1994 | Moll et al. | |
| 5,366,478 A * | 11/1994 | Brinkerhoff | A61B 17/3423 248/56 |
| 5,454,367 A | 10/1995 | Moll et al. | |
| 5,496,359 A | 3/1996 | Davidson | |
| 5,514,153 A | 5/1996 | Bonutti | |
| 5,522,790 A | 6/1996 | Moll et al. | |
| RE35,312 E | 8/1996 | Christoudias | |
| 5,545,179 A * | 8/1996 | Williamson, IV | A61B 17/3423 600/32 |
| 5,575,759 A | 11/1996 | Moll et al. | |
| 5,588,951 A | 12/1996 | Zhu et al. | |
| 5,601,589 A | 2/1997 | Fogarty et al. | |
| 5,632,761 A | 5/1997 | Smith et al. | |
| 5,634,937 A * | 6/1997 | Mollenauer et al. | 606/213 |
| 5,656,013 A | 8/1997 | Yoon | |
| 5,693,029 A | 12/1997 | Leonhardt | |
| 5,865,728 A | 2/1999 | Moll et al. | |
| 5,967,970 A * | 10/1999 | Cowan et al. | 600/207 |
| 6,033,428 A * | 3/2000 | Sardella | A61B 17/3423 606/213 |
| 6,146,401 A | 11/2000 | Yoon et al. | |
| 6,176,873 B1 * | 1/2001 | Ouchi | 623/1.22 |
| 6,361,546 B1 | 3/2002 | Khosravi | |
| 6,428,550 B1 * | 8/2002 | Vargas | A61B 17/11 606/151 |
| 6,451,042 B1 | 9/2002 | Bonutti | |
| 6,527,789 B1 | 3/2003 | Lau et al. | |
| 6,572,629 B2 | 6/2003 | Kalloo et al. | |
| 6,913,610 B2 | 7/2005 | Nakao | |
| 6,988,987 B2 | 1/2006 | Ishikawa et al. | |
| 7,186,262 B2 | 3/2007 | Saadat | |
| 7,214,237 B2 | 5/2007 | Don Michael et al. | |
| 7,717,923 B2 | 5/2010 | Kennedy, II et al. | |
| 7,877,132 B2 * | 1/2011 | Rongen et al. | 600/424 |
| 8,002,740 B2 * | 8/2011 | Willink | A61M 25/0084 604/96.01 |
| 8,517,933 B2 | 8/2013 | Mohr | |
| 8,771,180 B2 | 7/2014 | Mohr | |
| 2002/0049486 A1 | 4/2002 | Knudson et al. | |
| 2003/0208153 A1 * | 11/2003 | Stenzel | 604/60 |
| 2003/0216613 A1 | 11/2003 | Suzuki et al. | |
| 2004/0098081 A1 * | 5/2004 | Landreville | H01Q 3/2676 623/1.11 |
| 2004/0122456 A1 | 6/2004 | Saadat et al. | |
| 2004/0143286 A1 | 7/2004 | Johnson et al. | |
| 2004/0249434 A1 * | 12/2004 | Andreas | A61F 2/856 623/1.11 |
| 2005/0059864 A1 * | 3/2005 | Fromovich et al. | 600/201 |
| 2005/0059865 A1 * | 3/2005 | Kahle et al. | 600/206 |
| 2005/0107664 A1 | 5/2005 | Kalloo et al. | |
| 2005/0113797 A1 * | 5/2005 | Ott | A61M 13/003 604/506 |
| 2006/0116749 A1 * | 6/2006 | Willink | A61M 25/0084 623/1.11 |
| 2006/0200003 A1 * | 9/2006 | Youssef | 600/207 |
| 2006/0287666 A1 | 12/2006 | Saadat et al. | |
| 2007/0032703 A1 * | 2/2007 | Sankaran et al. | 600/208 |
| 2007/0123840 A1 | 5/2007 | Cox | |
| 2007/0197896 A1 | 8/2007 | Moll et al. | |
| 2007/0239138 A1 | 10/2007 | Lawrence et al. | |
| 2007/0287889 A1 | 12/2007 | Mohr | |
| 2008/0086167 A1 * | 4/2008 | Mastri | A61B 17/3421 606/198 |
| 2009/0036744 A1 | 2/2009 | Vayser | |
| 2013/0253281 A1 * | 9/2013 | Piskun | A61B 17/3403 600/206 |
| 2015/0342638 A1 * | 12/2015 | Smith | A61B 17/00234 600/204 |

* cited by examiner

RETRACTION OF TISSUE FOR SINGLE PORT ENTRY, ROBOTICALLY ASSISTED MEDICAL PROCEDURES

CROSS REFERENCE TO RELATED APPLICATIONS

This application is a divisional of U.S. application Ser. No. 11/762,217, filed Jun. 13, 2007, now U.S. Pat. No. 8,517,933, which claims priority to U.S. Application No. 60/813,198, filed Jun. 13, 2006, each of which is incorporated herein by reference.

FIELD OF THE INVENTION

The present invention generally relates to the retraction of tissue during medical procedures and in particular, to apparatuses and methods for the retraction of tissue for single port entry, robotically assisted medical procedures.

BACKGROUND OF THE INVENTION

Medical robotic systems such as telesurgical systems used in performing minimally invasive surgical procedures offer many benefits over traditional open surgery techniques, including less pain, shorter hospital stays, quicker return to normal activities, minimal scarring, reduced recovery time, and less injury to tissue. Consequently, demand for such medical robotic systems is strong and growing.

Examples of medical robotic systems include the da Vinci® Surgical System and the da Vinci® S™ Surgical System from Intuitive Surgical, Inc., of Sunnyvale, Calif. Each of these systems includes a surgeon's console, a patient-side cart, a high performance three-dimensional ("3-D") vision system, and Intuitive Surgical's proprietary EndoWrist® articulating instruments, which are modeled after the human wrist. When added to the motions of manipulators holding the surgical instruments, these articulating instruments allow at least six degrees of freedom of motion to their end effectors, which is comparable to or even greater than the natural motions of open surgery.

In conventional medical robotic systems, each medical device such as a surgical tool or image capturing device is typically manipulated by a separate robotic arm and is directed to a surgical site within a patient through its own minimally invasive incision. When it is desirable to retract extraneous tissue in order to access a target tissue to perform a medical procedure, it may be a simple matter to employ an extra robotic arm or human assistant to manipulate a retractor, such as shown in FIGS. 1~2, where instruments 101, 102 gain clear physical access and image capturing device 103 gains clear visible access to target tissue 104 by employing a conventional retractor 201 which is used to pull extraneous tissue 105 out of their way.

When only a single entry port is available for performing a medical procedure, however, retraction of extraneous tissue is not so simple a matter. First of all, the medical device in such case may be a surgical instrument that includes more than one surgical tool as well as possibly an image capturing device that are controllably extendable and manipulatable: out of a distal end of the surgical instrument. If the retractor is a separate tool, then trying to fit it through the same port as the surgical instrument is generally not feasible due to the limited size of the port (which may be an incision or a natural body orifice).

On the other hand, adding a retractor as an additional surgical tool to the single port entry surgical instrument so that the additional tool is also controllably extendable and manipulatable out of the distal end of the surgical instrument is also not generally feasible due again to the limited diameter of the single port entry which in turn, places a limit on the maximum diameter of the surgical instrument. Even if it were feasible to add the retractor as an additional tool to the surgical instrument, it may not be possible for the retractor to physically reach the tissue to be retracted while the other surgical tools are performing a medical procedure on the target tissue due to the physical coupling, of the tools of the surgical instrument. In addition, even if the retractor tool was able to reach the extraneous tissue and have sufficient available extension to move it out of the way, it may be difficult for the retractor to exert the necessary force to do so because of a lack of leverage in its construction.

OBJECTS AND SUMMARY OF THE INVENTION

Accordingly, one object of one or more aspects of the present invention is a device for retracting tissue during a medical procedure performed using only a single port entry in the patient's body.

Another object of one or more aspects of the present invention is a method for retracting tissue during a medical procedure performed using only a single port entry in the patient's body.

These and additional objects are accomplished by the various aspects of the present invention, wherein briefly stated, one aspect is a surgical instrument comprising: an elongated structure having proximal and distal ends and a first lumen extending between the proximal and distal ends; a surgical tool inserted within the first lumen, wherein the surgical tool has a distal end adapted with an end effector and a proximal end adapted with an interface for controllably manipulating the end effector for performing a medical procedure; a balloon disposed around an outer surface of the elongated structure; and an expandable retractor disposed around an outer surface of the balloon so that the expandable retractor is expanded and locks in an expanded configuration when the balloon is expanded to sufficient volume.

Another aspect is a method for retracting extraneous tissue using a surgical instrument configured with a balloon disposed around the surgical instrument so that the surgical instrument extends within a core formed in the balloon, and an expandable retractor disposed around the balloon so that the expandable retractor is expanded and locks in an expanded configuration when the balloon is expanded to sufficient volume, comprising: robotically positioning the surgical instrument so that the expandable retractor retracts the extraneous tissue when the expandable retractor is expanded to and locked in its expanded configuration; expanding the balloon so that the expandable retractor is expanded to and locked in its expanded configuration; deflating the balloon; and robotically moving an end effector of the surgical instrument towards a target tissue while the expanded retractor remains locked and in place so as to continue retracting the extraneous tissue.

Another aspect is a method for securing an entry port for a surgical instrument through an anatomic structure, wherein the surgical instrument is configured with a tubular-shaped balloon disposed around the surgical instrument so that the surgical instrument extends within a core formed in the tubular-shaped balloon, and a retractor disposed around the tubular-shaped balloon in an unexpanded configuration having an outer diameter less than an inner diameter of the entry port and expandable so that the retractor is expanded and locks in an expanded configuration having an outer diameter slightly more than the inner diameter of the entry port when the tubular-shaped balloon is expanded to sufficient volume, comprising: robotically positioning the surgical instrument so that the retractor in its unexpanded configuration is approximately centered in the entry port; expanding the tubular-shaped balloon so that the retractor is expanded to and locked in its expanded configuration; deflating the tubular-shaped balloon; and robotically moving the surgical instrument towards a target tissue while the retractor remains in its expanded configuration to secure the entry port.

Another aspect is a method for sealing an entry port for a surgical instrument through an anatomic structure, wherein the surgical instrument is configured with a tubular-shaped balloon disposed around the surgical instrument so that the surgical instrument extends within a core formed in the tubular-shaped balloon, comprising: robotically positioning the surgical instrument so that the tubular-shaped balloon in its unexpanded configuration is approximately centered in the entry port; and expanding the tubular-shaped balloon so that the expanded tubular-shaped balloon forms a seal around the entry port; and robotically moving an end effector of the surgical instrument towards a target tissue for performing a medical procedure on the target tissue using the end effector.

Additional objects, features and advantages of the various aspects of the present invention will become apparent from the following description of its preferred embodiment, which description should be taken in conjunction with the accompanying drawings.

DETAILED DESCRIPTION OF THE PREFERRED EMBODIMENT

Figure 1:
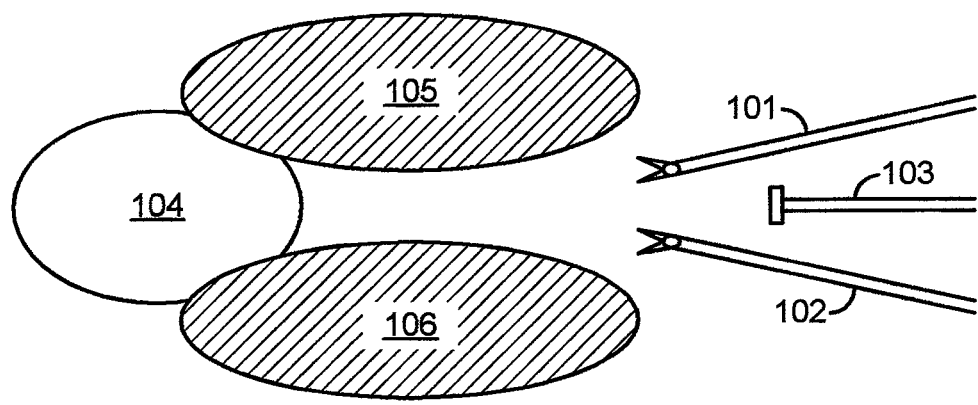
FIGS. 1~2 illustrate simplified top views of a surgical site before and after performing conventional retraction of extraneous tissue.
Figure 2:
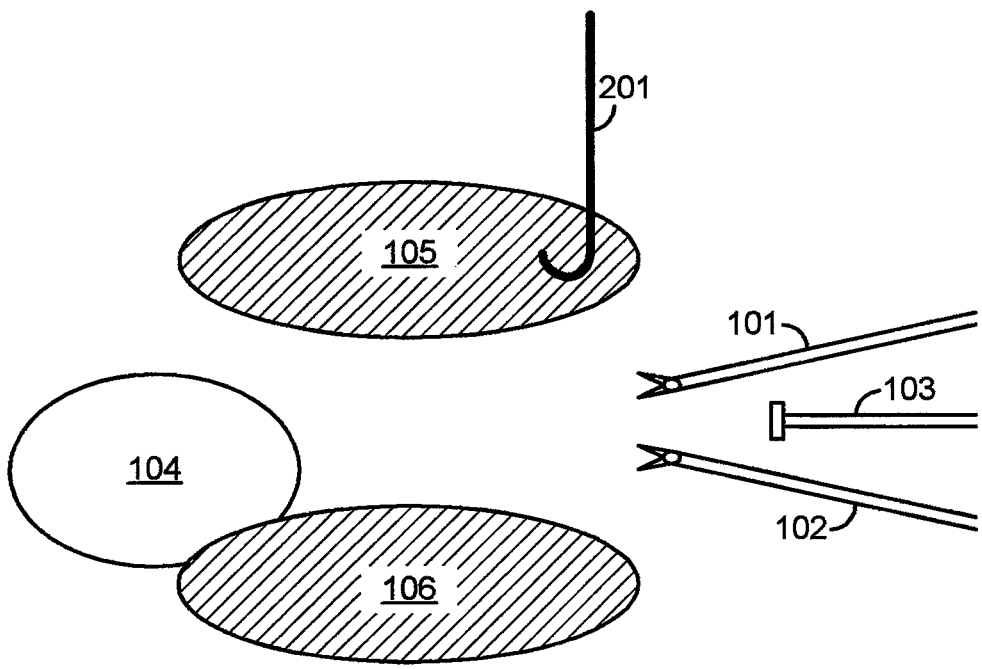
Figure 3:
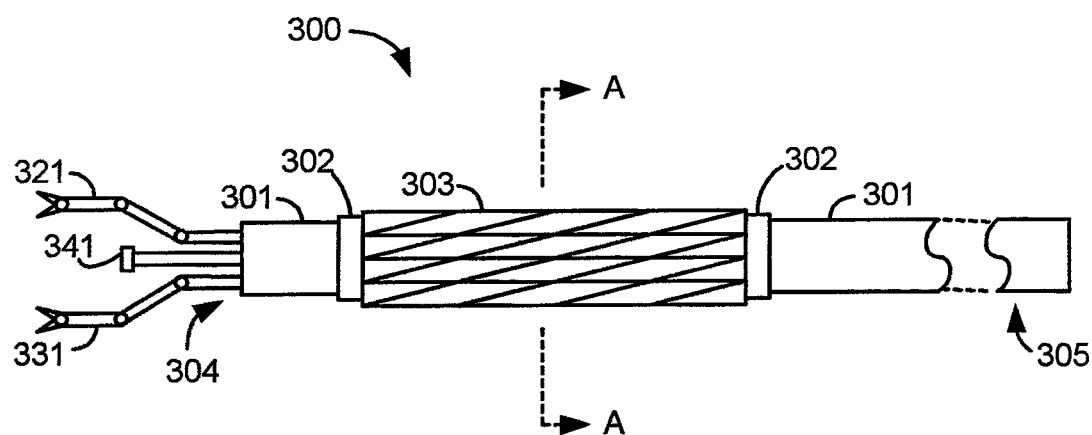
FIGS. 3~4 illustrate simplified top and cross-sectional views of a surgical instrument with a balloon expandable retractor utilizing aspects of the present invention.
Figure 4:
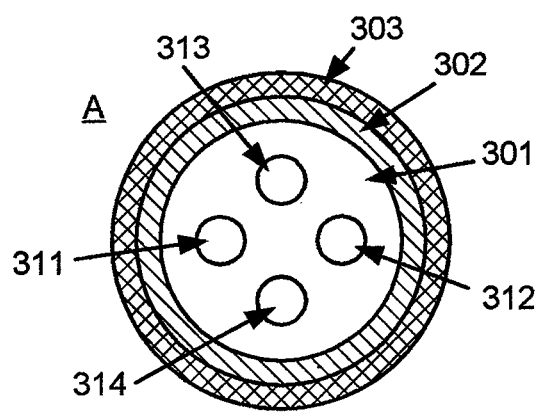
Figure 5:
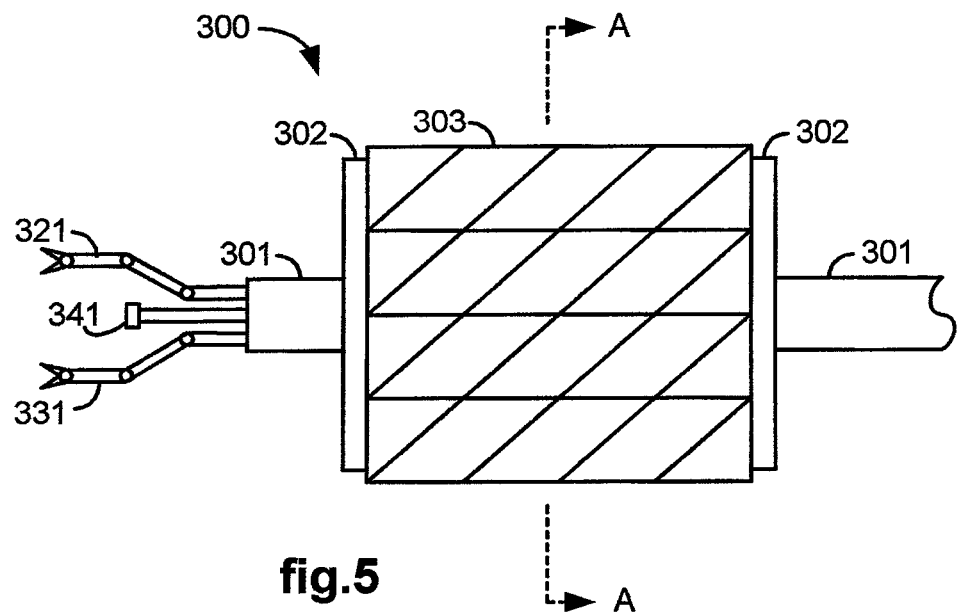
FIGS. 5~6 illustrate simplified top and cross-sectional views of a surgical instrument with a balloon expanded retractor utilizing aspects of the present invention.
Figure 6:
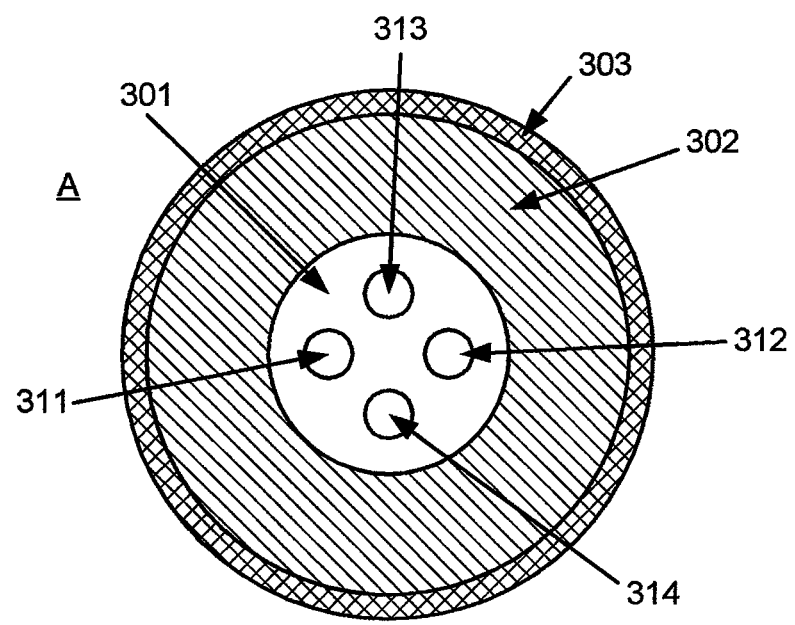
Figure 7:
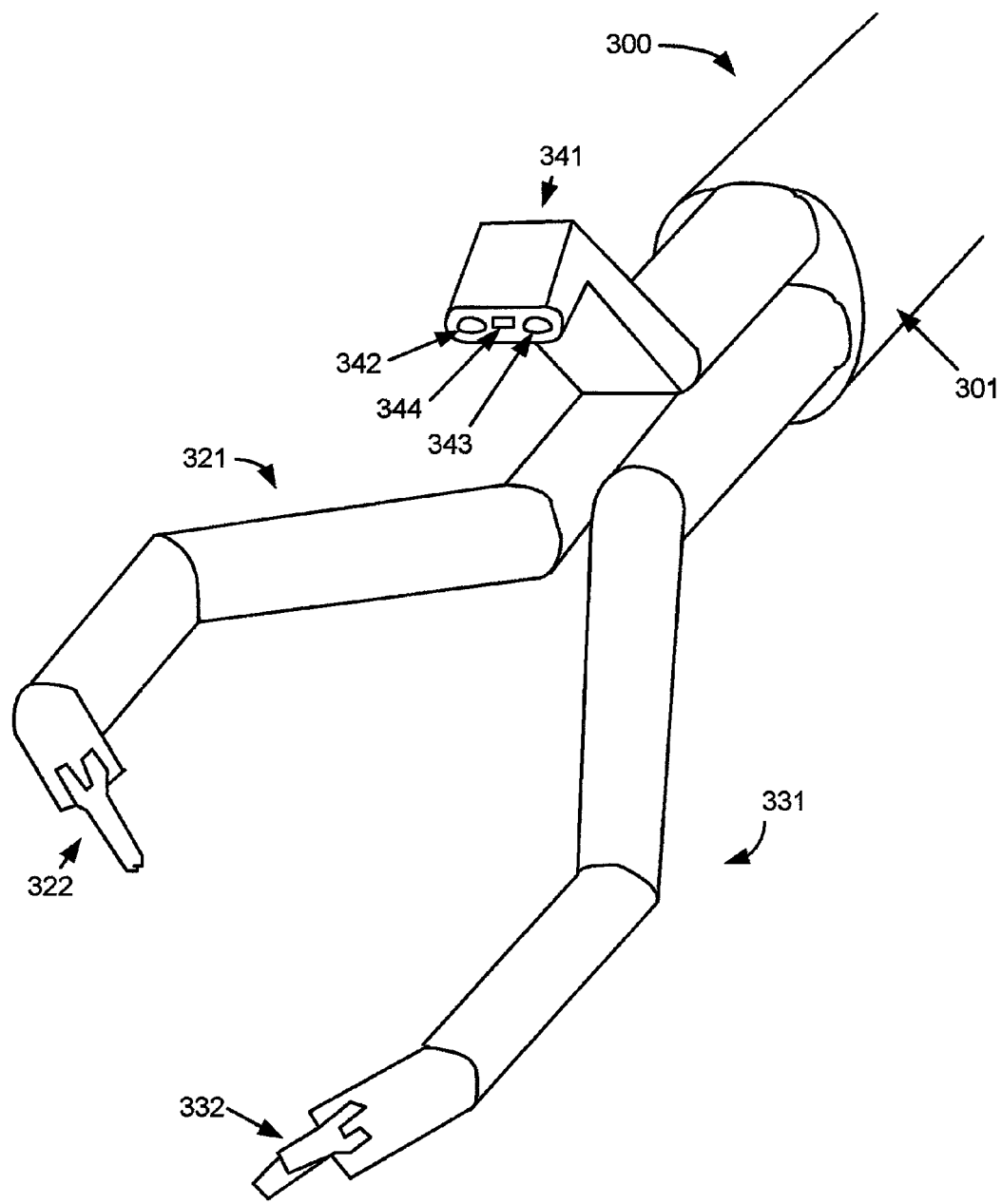
FIG. 7 illustrates a perspective view of a distal end of a surgical instrument utilizing aspects of the present invention.

FIGS. 3~7 illustrate simplified examples of various views of a surgical instrument 300 adapted for single port entry into a patient for performing a medical procedure on target tissue. In particular, FIGS. 3~4 illustrate top and cross-sectional views of the surgical instrument 300 in its deflated balloon and collapsed retractor configuration, FIGS. 5~6 illustrate top and cross-sectional views of the surgical instrument 300 in its expanded balloon and retractor configuration, and FIG. 7 illustrates a perspective view of a distal end 304 of the surgical instrument 300.

The surgical instrument 300 includes an elongated structure 301 (also referred to herein as a "tool guide" or an "elongated tool guide structure") having a generally convex cross-section such as a cylinder. A balloon 302 is disposed around the elongated structure 301 and is tubular in shape so that when it is deflated, the elongated structure 301 snugly fits in a central core of the tubular-shaped balloon 302. An expandable retractor 303 is disposed around the tubular-shaped balloon 302. The retractor 303 is preferably like a hollow cylinder in shape so that when it is collapsed, the tubular-shaped balloon 302 fits snugly in the hollow of the retractor 303. The retractor 303 is further constructed so that as the balloon 302 inflates, the retractor 303 expands accordingly, like an expandable stent, until the balloon 302 reaches a certain volume, at which time the retractor 303 locks in its expanded configuration where it no longer expands and remains at that expansion size even after the balloon 302 is deflated and the retractor 303 is no longer in physical contact with the rest of the surgical instrument 300.

The tool guide 301 has a plurality of lumens 311~314 extending between its distal and proximal ends 304, 305. The lumens 311-314 shown in FIGS. 4, 6 are illustrative of various diameters and geometric cross sections. In an exemplary configuration, a pair of surgical tools 321, 331 are inserted in lumens 311, 312, and an image capturing device 341 inserted in lumen 313. The surgical tools 321, 331 have distal ends adapted with end effectors 322, 332, and proximal ends adapted with interfaces (not shown) for control purposes. The image capturing device 341 has a distal end adapted with a stereoscopic camera pair 342, 343 and a light emitter 344, and it has a proximal end adapted with an interface (not shown) for control as well as image capturing, processing and transmission purposes.

The interfaces for the surgical tools 321, 331 and the image capturing device 341 are coupled to one or more processors in a medical robotic system so that the surgical tools 321, 331 (and their end effectors) may be robotically manipulated by a surgeon using hand-manipulated input control devices (i.e., teleoperated) while viewing three-dimensional (3-D) images of the surgical site as captured by the image capturing device 341 and viewed on a 3-D monitor, such as generally described, for example, in commonly owned U.S. Pat. No. 6,671,581 "Camera Referenced Control in a Minimally Invasive Surgical Apparatus," which is incorporated herein by reference, with the exception that the surgical tools 321, 331 and the image capturing device 341 all enter the patient through a single entry port as part of the surgical instrument 300 rather than through individually assigned entry ports as described in the reference.

Figure 8:
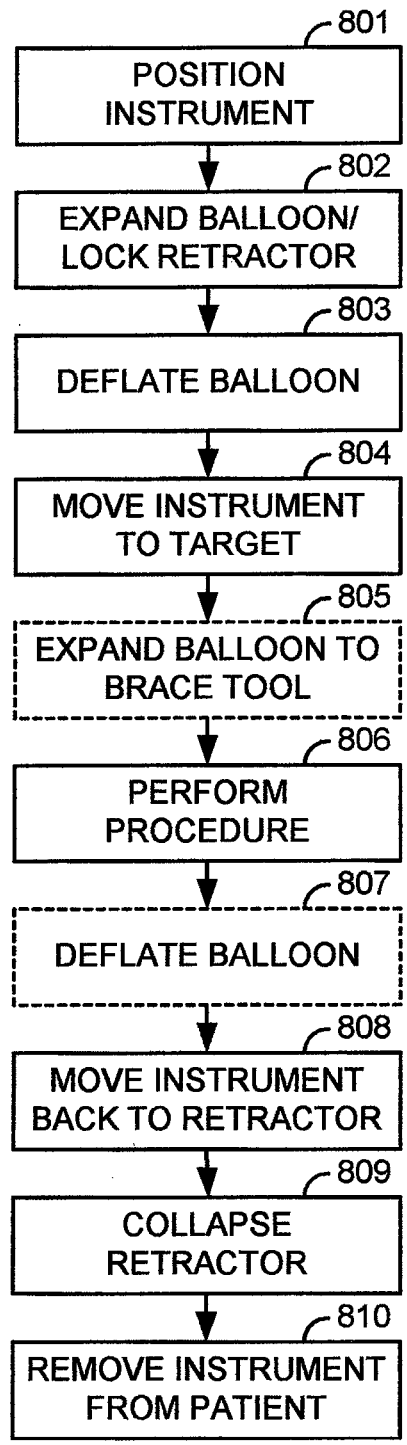
FIG. 8 illustrates a flow diagram of a method for retracting tissue using a surgical instrument with a balloon expandable retractor, utilizing aspects of the present invention.

FIG. 8 illustrates, as an example, a flow diagram of a method for retracting tissue using the surgical instrument 300, and FIGS. 9~14 illustrate, as an aid in describing the method, simplified top views of the surgical site as the surgical instrument 300 deploys its balloon-expandable retractor 303 to perform a medical procedure.

Figure 9:
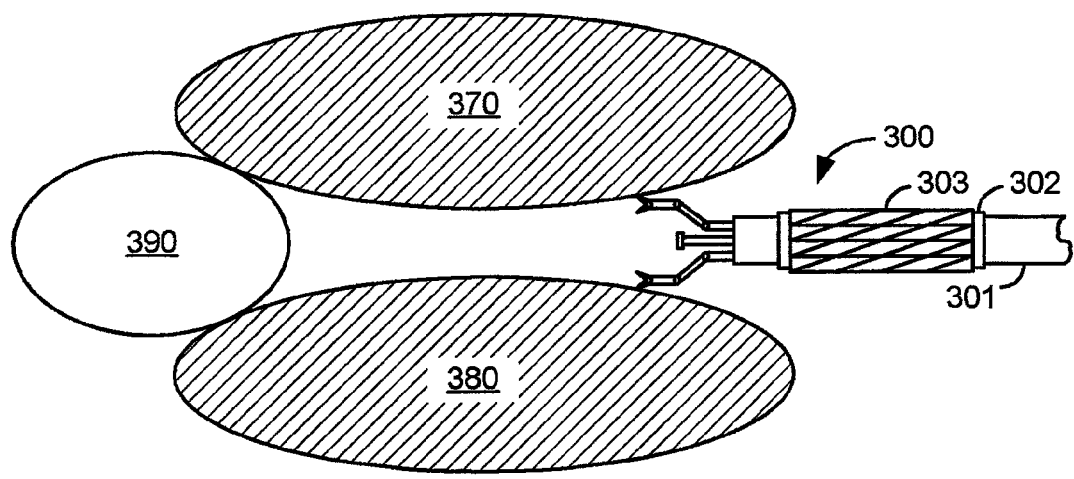
FIGS. 9~14 illustrate simplified top views of a surgical site as a surgical instrument, which is adapted with a balloon expandable retractor utilizing aspects of the present invention, deploys its retractor for performing a medical procedure.

In 801, the surgical instrument 300, in its unexpanded configuration as shown and described in reference to FIGS. 3~4, is robotically moved towards the target tissue 390 as shown in FIG. 9, and positioned adjacent extraneous tissue 370, 380 which are to be retracted in order to provide accessibility to and/or better visibility of the target tissue 390.

Figure 10:
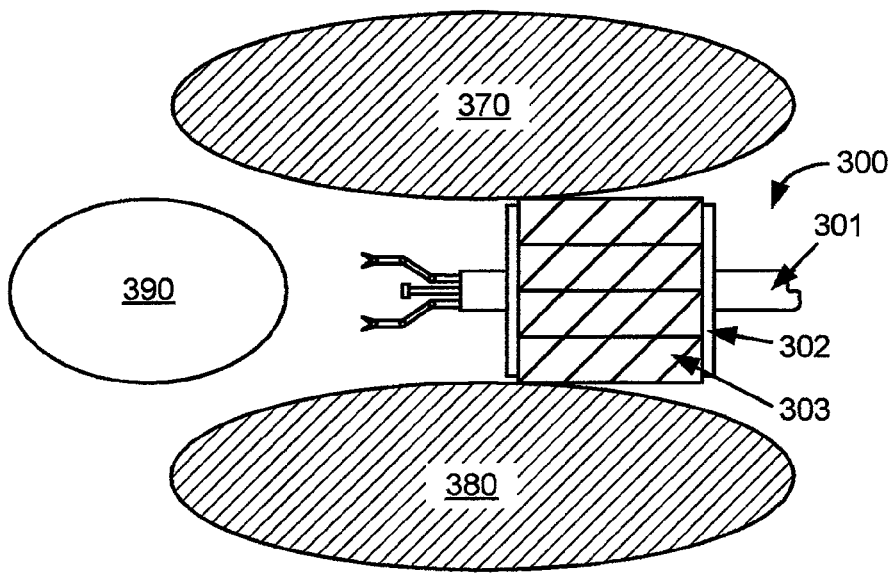

In 802, once the surgical instrument 300 is properly positioned for retraction of the extraneous tissue 370, 380, the balloon 302 is expanded by filling it with a gas or liquid using a tube (not shown) running, e.g., along the outer surface of the surgical instrument 300 and connected to a gas or liquid source (not shown). In turn the expanding balloon 302 causes the retractor 303 to expand and lock in its expanded configuration after the balloon 302 reaches sufficient volume, as shown and described in reference to FIGS. 5~6. Consequently, retractor 303 retracts the extraneous tissue 370, 380 by spreading them apart as shown in FIG. 10. At this point, the forcing apart of the extraneous tissue 370, 380 results in counter forces that may hold the expanded retractor 303 in place even after the balloon 302 is deflated and the expanded retractor 303 is no longer in physical contact with the rest of the surgical instrument 300.

Figure 11:
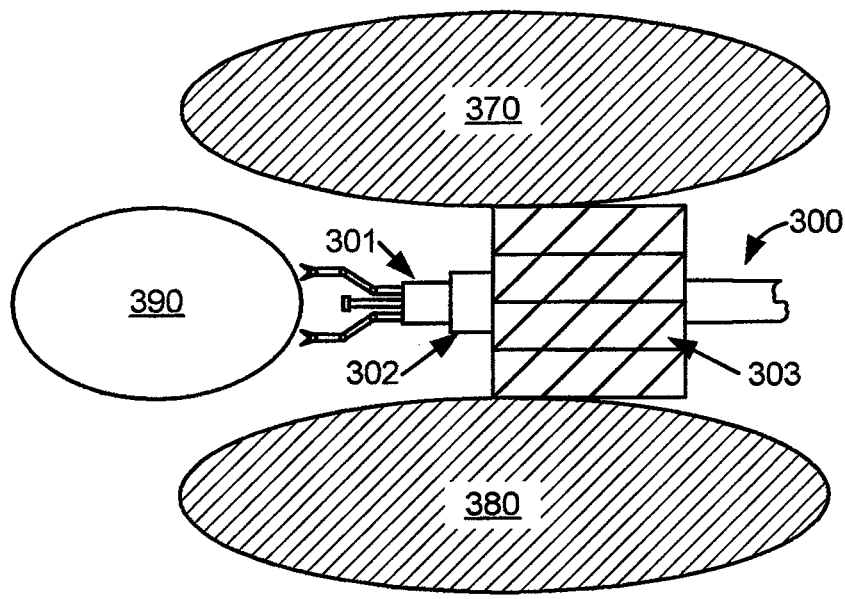
Figure 12:
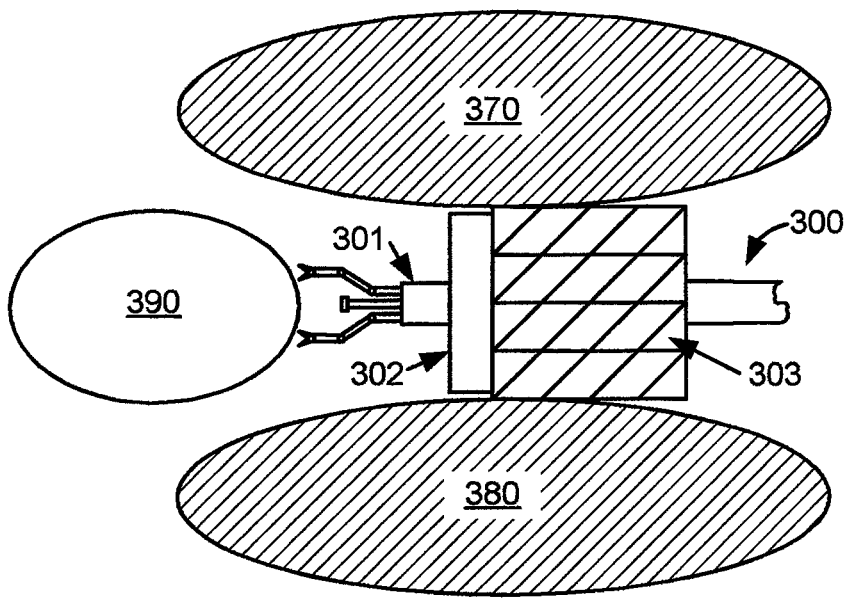

In 803, the balloon is deflated and in 804, the surgical instrument 300 is moved towards the target tissue 390 while leaving the expanded and locked retractor 303 in place so as to continue retracting tissue 370, 380, as shown in FIG. 11. Once the surgical instrument 300 is in proper position to perform the medical procedure on the target tissue 390, in 805, the balloon 302 may optionally be re-inflated so that at least part of it is being forced against the inner surface of the expanded retractor 303, such as shown in FIG. 12. In this way, the retractor 303 now additionally serves as a brace for the rest of the surgical instrument 300 and in particular, provides a stable platform for its surgical tools 321, 331 and image capturing device 341 during the performance of the medical procedure.

In 806, the end effectors of the surgical tools 321, 331 are robotically manipulated by the surgeon to perform the medical procedure on the target tissue 390 while viewing a monitor in which captured images from the image capturing device 341 are viewed. To enhance the quality, contrast, and or color of the images being captured, the outer surface of the balloon 302 may have a mirror-like or highly reflective coating such as conventionally used for reflectors in photography. This highly reflective coating serves to re-reflect light originating at light emitter 344, which is then reflected by surrounding tissue, back towards the target tissue 390.

Figure 13:
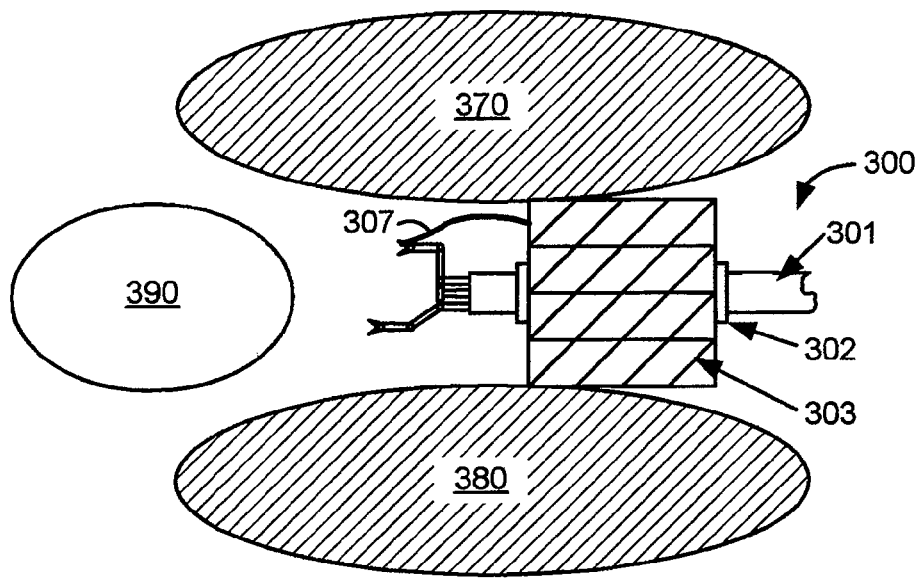

Once the medical procedure is completed, if the balloon was previously inflated in 805, then in 807, it is deflated. In 808, the surgical instrument 300 is moved back towards the expanded retractor 303, and in 809, the expanded retractor 303 is unlocked and collapsed. As an example of this last procedure, FIG. 13 illustrates an end effector of one of the surgical tools 321, 331 grabbing and pulling on a string 307 (or other extending element) which is attached to the retractor 303 and used for causing the expanded retractor 303 to collapse by, for example, collapsing a key strut which keeps the retractor 303 in its locked configuration.

Figure 14:
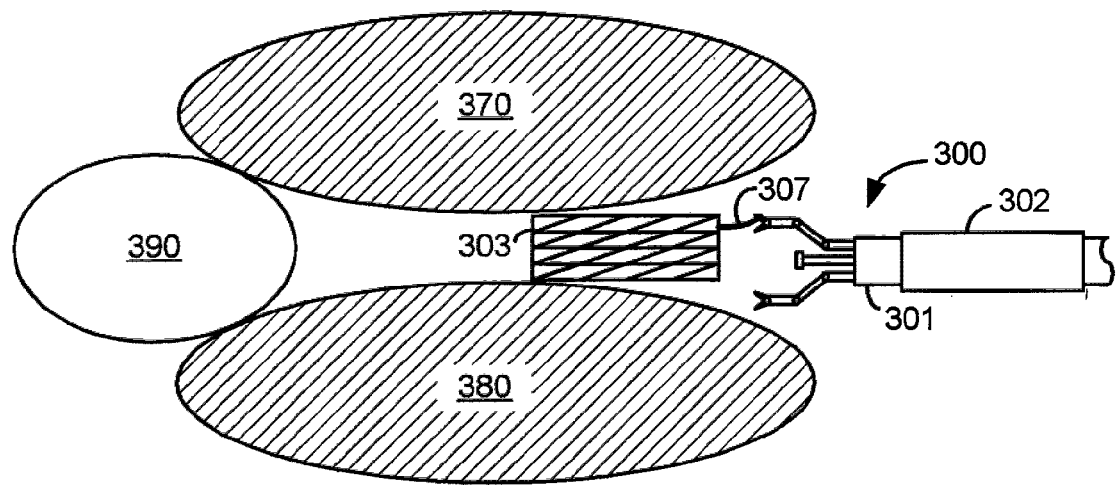

In 810, the surgical instrument 300 is then robotically removed from the patient in a conventional manner with the end effector still grasping the string 307 so that the collapsed retractor 303 may be pulled out via the incision or natural orifice in a manner similar to removing a tissue capture bag, as shown in FIG. 14.

As an alternative to collapsing the expandable retractor 303 so that it can be removed along with the surgical instrument 300, as described in reference to 809~810 of FIG. 8, the retractor 303 may be left in its expanded configuration in the patient if it is formed of a biodegradable or bioabsorbable material and it is left in a part of the body that allows it to dissolve naturally over time, or if it is formed of a material that is non-absorbable until exposed to an activator chemical which breaks down the material allowing controlled dissolution and it is left in a part of the body where the activator chemical can be safely introduced.

Figure 15:
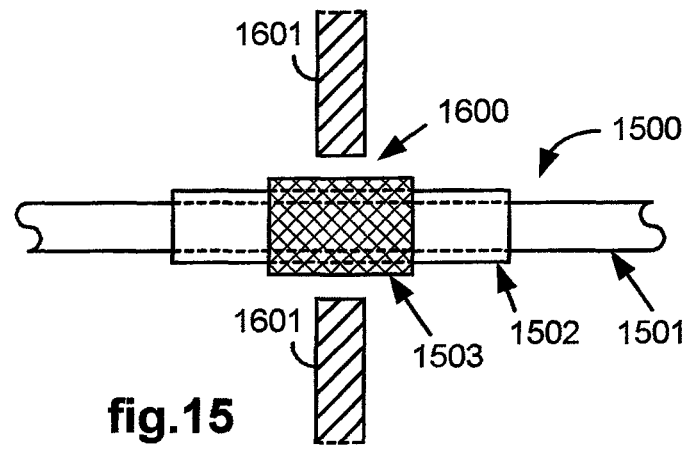
FIGS. 15~17 illustrate simplified side views of an entry port to a cavity of a patient's body as a surgical instrument deploys a retractor to secure the entry port, utilizing aspects of the present invention.
Figure 16:
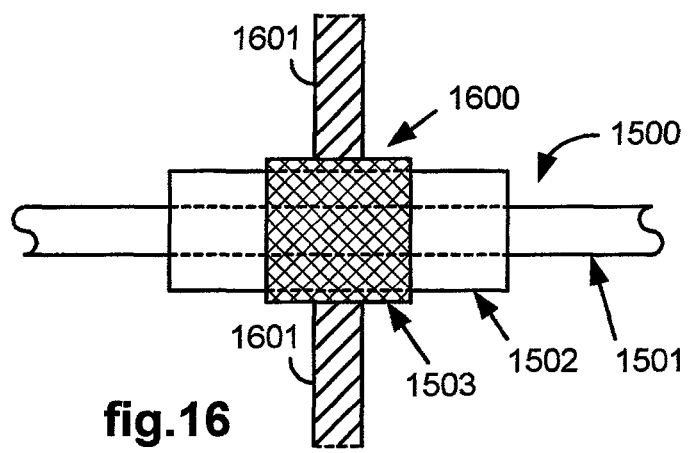
Figure 17:
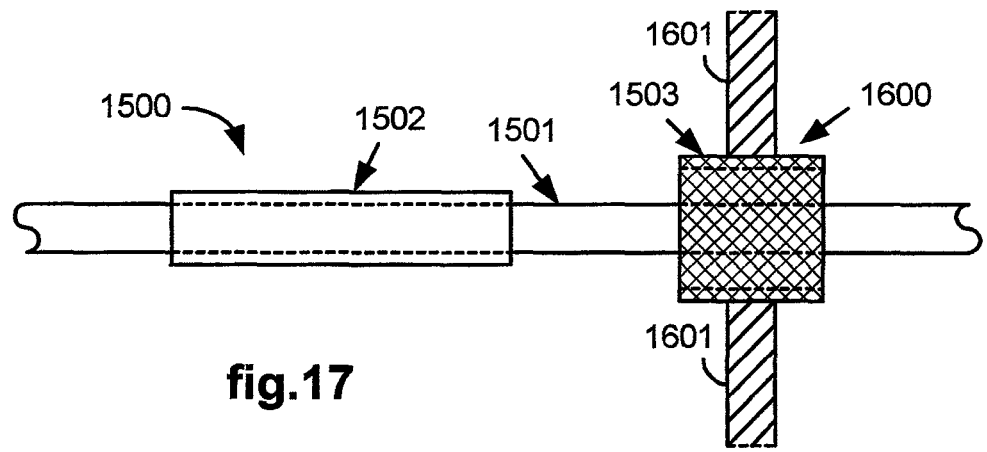

A method for securing an entry port 1600 (natural or surgically formed) for a surgical instrument 1500 through an anatomic structure 1601 is illustrated by FIGS. 15~17, in which simplified side views of the entry port 1600 to a cavity or other area of a patient's body are illustrated as the surgical instrument 1500 deploys an expandable retractor 1503 to secure and protect the entry port 1600, such as a cannula secures and protects an incision in a patient's body when installed for performing laparoscopic surgery. As just one example of its use, procedures involving transluminal incisions and passage may benefit from such stenting protection.

Starting with FIG. 15, the surgical instrument 1500 is shown being robotically positioned within the entry port 1600 so that its retractor 1503 is approximately centered in the entry port 1600. As shown in FIG. 16, a tubular-shaped balloon 1502 disposed around an elongated tool guide structure 1501 of the surgical instrument 1500 is then expanded, which in turn causes the retractor 1503, which is disposed around the balloon 1502, to expand and be locked in its expanded configuration, in a manner substantially the same as described in reference to 802 of FIG. 8. The cross-sectional diameter of the retractor 1503 in its expanded configuration is designed in this case so as to be slightly larger than the diameter of the entry port 1600 so as to ensure that the expanded retractor 1503 remains firmly in the entry port 1600 thereby appearing and functioning as a grommet. As shown in FIG. 17, the balloon 1502 is then deflated and the surgical instrument 1500 robotically moved towards a surgical site within the patient, leaving the retractor 1503 firmly entrenched in the entry port 1600 so as to secure it to make sure that it remains open and protected as the surgical instrument 1500 enters, passes through and exits the entry port 1600 during the process of performing a medical procedure on a patient. Removal of the retractor 1503 may be performed by collapsing and subsequently removing it, such as described, for example, in reference to 808~809 of FIG. 8.

Figure 18:
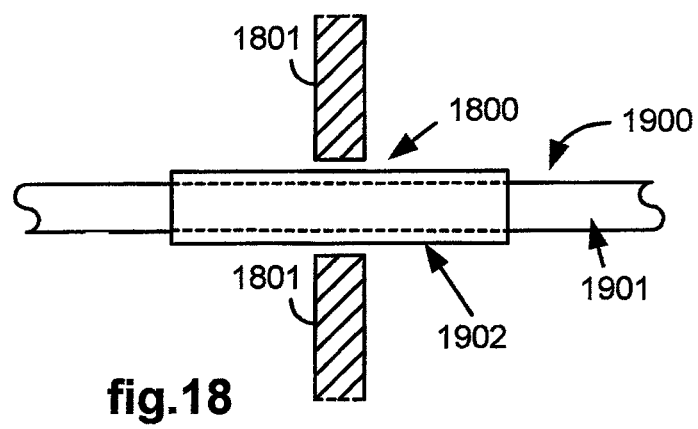
FIGS. 18~19 illustrate simplified side views of an entry port to a cavity of a patient's body as a surgical instrument deploys a balloon to seal the entry port, utilizing aspects of the present invention.
Figure 19:
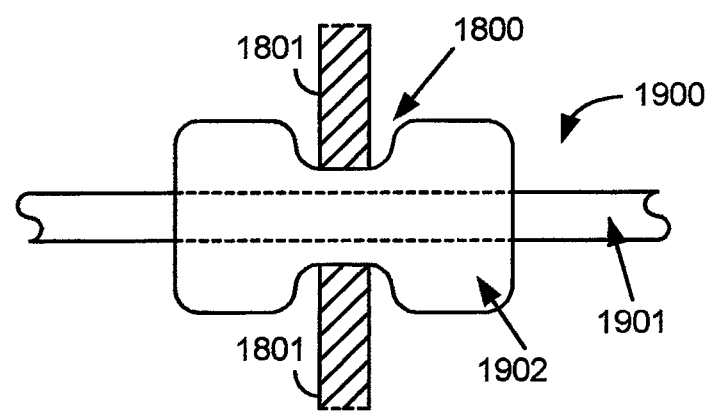

A method for sealing an entry port 1800 through an anatomic structure 1801 is illustrated by FIGS. 18~19, in which simplified side views of the entry port 1800 to a cavity of a patient's body are illustrated as the surgical instrument 1900 deploys a balloon 1902 to seal the entry port 1800. Starting with FIG. 18, the surgical instrument 1900 is shown as being robotically positioned within the entry port 1800 so that its tubular or other suitably shaped, deflated balloon 1902 is approximately centered in the entry port 1800. As shown in FIG. 19, the balloon 1902 is then expanded (using a gas or liquid tube extending along the length of the surgical instrument 1900 to an external gas or liquid source) so as to form an air-tight or fluid-tight seal around the entry port 1800. The body cavity may then be insufflated with a gas provided through a lumen formed within the elongated tool guide structure 1901 or a tube extending along its length. The surgical instrument 1900 may also be extended forward to a surgical site within the patient with the inner surface of the expanded balloon 1902 sliding along the outer surface of elongated tool guide structure 1901. Alternatively, only its end effector may be robotically extended forward with the elongated tool guide structure 1901 remaining in place. Subsequent removal of the balloon 1902 may be performed after the medical procedure by deflating it so that it collapses back onto the elongated structure 1901 allowing it to pass through the entry port 1800 and be removed with the surgical instrument 1900.

Although the various aspects of the present invention have been described with respect to a preferred embodiment, it will be understood that the invention is entitled to full protection within the full scope of the appended claims.

I claim:

1. A method for securing an entry port through an anatomic structure for a surgical instrument before moving a tool guide forward towards a target tissue, wherein the surgical instrument includes the tool guide, a tubular-shaped balloon, and a retractor, wherein the tubular-shaped balloon is disposed around the tool guide so that the tool guide extends within a core formed in the tubular-shaped balloon, wherein the retractor is disposed around the tubular-shaped balloon in an unexpanded configuration while the tubular-shaped balloon is in a deflated condition in which an outer diameter of the tubular-shaped balloon is less than an inner diameter of the entry port, wherein the retractor is constructed so that the retractor is expanded and locks in an expanded configuration when the tubular-shaped balloon is in an inflated condition that causes an outer diameter of the retractor to be pressed against and held in place by an inner wall of the entry port, and wherein the retractor is constructed so that the retractor remains locked without external support when the tubular-shaped balloon is deflated and no longer contacts an inner surface of the retractor, the method comprising:
    manipulating a tool inserted in the tool guide to cut a hole through the anatomic structure so as to form the entry port prior to disposing the retractor within the entry port;
    securing the entry port through the anatomic structure by:
        positioning the surgical instrument so that the retractor in its unexpanded configuration is disposed within the entry port;
        expanding the tubular-shaped balloon so that the retractor is expanded to and locked in its expanded configuration so that the outer diameter of the retractor is pressed against and held in place by the inner wall of the entry port; and
        deflating the tubular-shaped balloon so that the tubular-shaped balloon no longer contacts the inner surface of the retractor while the retractor remains locked in its expanded configuration without external support to secure the entry port; and
    moving the tool guide forward towards the target tissue while the retractor, which is locked in its expanded configuration, is securing the entry port, wherein the target tissue is disposed so that the surgical instrument had not passed by or through the target tissue prior to positioning the surgical instrument so that the retractor in its unexpanded configuration is disposed within the entry port.

2. A method for securing an entry port through an anatomic structure for a surgical instrument before moving a tool guide forward towards a target tissue, wherein the surgical instrument includes the tool guide, a tubular-shaped balloon, and a retractor, wherein the tubular-shaped balloon is disposed around the tool guide so that the tool guide extends within a core formed in the tubular-shaped balloon, wherein the retractor is disposed around the tubular-shaped balloon in an unexpanded configuration while the tubular-shaped balloon is in a deflated condition in which an outer diameter of the tubular-shaped balloon is less than an inner diameter of the entry port, wherein the retractor is constructed so that the retractor is expanded and locks in an expanded configuration when the tubular-shaped balloon is in an inflated condition that causes an outer diameter of the retractor to be pressed against and held in place by an inner wall of the entry port, and wherein the retractor is constructed so that the retractor remains locked without external support when the tubular-shaped balloon is deflated and no longer contacts an inner surface of the retractor, the method comprising:
    securing the entry port through the anatomic structure by:
        positioning the surgical instrument so that the retractor in its unexpanded configuration is disposed within the entry port;
        expanding the tubular-shaped balloon so that the retractor is expanded to and locked in its expanded configuration so that the outer diameter of the retractor is pressed against and held in place by the inner wall of the entry port; and
        deflating the tubular-shaped balloon so that the tubular-shaped balloon no longer contacts the inner surface of the retractor while the retractor remains locked in its expanded configuration without external support to secure the entry port;
    moving the tool guide forward towards the target tissue while the retractor, which is locked in its expanded configuration, is securing the entry port, wherein the target tissue is disposed so that the surgical instrument had not passed by or through the target tissue prior to positioning the surgical instrument so that the retractor in its unexpanded configuration is disposed within the entry port;
    performing a medical procedure on the target tissue using a tool inserted in the tool guide;
    moving the tool guide and the tool back towards the entry port after performing the medical procedure; and
    manipulating the tool to interact with an element of the retractor so as to collapse the retractor from its expanded configuration.

3. The method of claim 2, wherein manipulating the tool to interact with the retractor so as to collapse the retractor from its expanded configuration, comprises:
    grasping and manipulating the element of the retractor by using an end effector of the tool, so that the manipulated element causes the retractor to collapse from its expanded configuration back to a non-expanded configuration.

* * * * *